(12) United States Patent
Haddach

(10) Patent No.: US 6,541,469 B2
(45) Date of Patent: Apr. 1, 2003

(54) CRF RECEPTOR ANTAGONISTS AND METHODS RELATING THERETO

(75) Inventor: Mustapha Haddach, San Diego, CA (US)

(73) Assignee: Neurocrine Biosciences, Inc., San Diego, CA (US)

(*) Notice: Subject to any disclaimer, the term of this patent is extended or adjusted under 35 U.S.C. 154(b) by 0 days.

(21) Appl. No.: 09/861,472

(22) Filed: May 18, 2001

(65) Prior Publication Data

US 2002/0032194 A1 Mar. 14, 2002

Related U.S. Application Data

(60) Provisional application No. 60/205,649, filed on May 18, 2000.

(51) Int. Cl.[7] .................... A61K 31/542; A61P 25/22; C07D 285/34; C07D 273/00; C07D 487/00
(52) U.S. Cl. ................ 514/222.8; 514/229.2; 514/243; 514/224.5; 544/9; 544/66; 544/184
(58) Field of Search ............. 514/224.5, 229.2, 514/243, 222.8; 544/9, 66, 184

(56) References Cited

U.S. PATENT DOCUMENTS 6,358,950 B1 * 3/2002 He et al. ................ 514/246

FOREIGN PATENT DOCUMENTS

| WO | WO 99/38868 | 8/1999 |
|----|-------------|--------|
| WO | WO 00/27850 | 5/2000 |

* cited by examiner

*Primary Examiner*—Mark L. Berch
*Assistant Examiner*—Tamthom N. Truong
(74) *Attorney, Agent, or Firm*—Seed IP Law Group PLLC

(57) ABSTRACT

CRF receptor antagonists are disclosed which have utility in the treatment of a variety of disorders, including the treatment of disorders manifesting hypersecretion of CRF in a warm-blooded animals, such as stroke. The CRF receptor antagonists of this invention have the following structure:

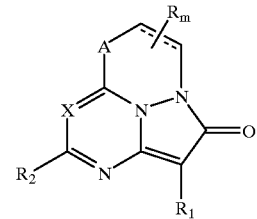

including stereoisomers and pharmaceutically acceptable salts thereof, wherein X is nitrogen or $CR_3$; A is O, S, or $NR_4$, and R, $R_1$, $R_2$ are as defined herein. Compositions containing a CRF receptor antagonist in combination with a pharmaceutically acceptable carrier are also disclosed, as well as methods for use of the same.

15 Claims, No Drawings

CRF RECEPTOR ANTAGONISTS AND METHODS RELATING THERETO

CROSS-REFERENCE TO RELATED APPLICATION

This application claims the benefit of U.S. Provisional Application No. 60/205,649 filed May 18, 2000.

TECHNICAL FIELD

This invention relates generally to CRF receptor antagonists, and to methods of treating disorders by administration of such antagonists to a warm-blooded animal in need thereof.

BACKGROUND OF THE INVENTION

The first corticotropin-releasing factor (CRF) was isolated from ovine hypothalmi and identified as a 41-amino acid peptide (Vale et al., *Science* 213:1394–1397, 1981). Subsequently, sequences of human and rat CRF were isolated and determined to be identical, but different from ovine CRF in 7 of the 41 amino acid residues (Rivier et al., *Proc. Natl. Acad. Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394–1397, 1981). Briefly, CRF is believed to initiate its biological effects by binding to a plasma membrane receptor which has been found to be distributed throughout the brain (DeSouza et al., *Science* 224:1449–1451, 1984), pituitary (DeSouza et al., *Methods Enzymol.* 124:560, 1986; Wynn et al., *Biochem. Biophys. Res. Comm.* 110:602–608, 1983), adrenals (Udelsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118:1171–1179, 1986) which mediates CRF-stimulated increase in intracellular production of cAMP (Bilezikjian, L. M., and W. W. Vale, *Endocrinology* 113:657–662, 1983). The receptor for CRF has now been cloned from rat (Perrin et al., *Endo* 133(6):3058–3061, 1993), and human brain (Chen et al., *PNAS* 90(19):8967–8971, 1993; Vita et al., *FEBS* 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J. Physiol.* 255:R744, 1988). Furthermore, clinical data suggests that CRF may be hypersecreted in the brain in depression, anxiety-related disorders, and anorexia nervosa. (DeSouza, *Ann. Reports in Med. Chem.* 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyrazoline derivatives (Abreu et al., U.S. Pat. No. 5,063,245) and substituted 2-aminothiazole derivatives (Courtemanche et al., Australian Patent No. AU-A-41399/93) have been reported as CRF receptor antagonists. These particular derivatives were found to be effective in inhibiting the binding of CRF to its receptor in the 1–10 μM range and 0.1–10 μM range, respectively.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structure (I):

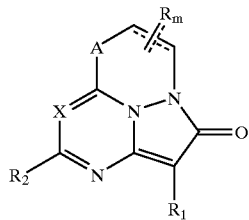

(I)

including stereoisomers, prodrugs and pharmaceutically acceptable salts thereof, wherein m, R, $R_1$, $R_2$, A and X are as defined below.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists.

In a first embodiment, the CRF receptor antagonists of this invention have the following structure (I):

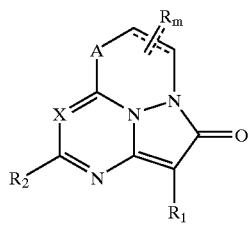

(I)

including stereoisomers, prodrugs and pharmaceutically acceptable salts thereof,
wherein:
X is nitrogen or $CR_3$;
A is O, S or $NR_4$;
"---" represents an optional double bond;
R is an optional substituent which, at each occurrence, is independently alkyl, aryl, heteroaryl, alkylidenyl, arylalkyl or heteroarylalkyl, wherein m is 0, 1, 2 or 3 and represents the number of R substituents; wherein, when R is a monovalent substituent, it is single-bonded to the ring, and when R is a divalent substituent, it is double-bonded to the ring.
$R_1$ is alkyl, substituted alkyl, aryl, substituted aryl, heteroaryl or substituted heteroaryl;
$R_2$ is hydrogen, halogen, cyano, alkyl, substituted alkyl, alkoxy or thioalkyl;
$R_3$ is hydrogen, halogen, alkyl or substituted alkyl; and
$R_4$ is hydrogen, alkyl, substituted alkyl, aryl, substituted aryl, heterocycle or substituted heterocycle.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl, Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. "Alkylidenyl" represents a divalent alkyl from which two hydrogen atoms are taken from the same carbon atom, such as =CH$_2$, =CHCH$_3$, =CHCH$_2$CH$_3$, =C(CH$_3$)CH$_2$CH$_3$, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl (i.e., —CH$_2$phenyl), —CH$_2$-(1 or 2-naphthyl), —(CH$_2$)$_2$phenyl, —(CH$_2$)$_3$phenyl, —CH(phenyl)$_2$, and the like.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The term "substituted" as used herein means any of the above groups (i.e, alkyl, aryl, arylalkyl, heteroaryl, heteroarylalkyl, heterocycle and heterocyclealkyl) wherein at least one hydrogen atom is replaced with a substituent. In the case of a keto substituent ("—C(=O)—") two hydrogen atoms are replaced. "Substituents" within the context of this invention include halogen, hydroxy, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, NR$_a$C(=O) NR$_a$R$_b$, —NR$_a$C(=O)OR$_b$ —NR$_a$SO$_2$R$_b$, —OR$_a$, —C(=O)R$_a$ —C(=O)OR$_a$, —C(=O)NR$_a$R$_b$, —OC(=O) NR$_a$R$_b$, —SH, —SR$_a$, —SOR$_a$, —S(=O)$_2$R$_a$, —OS(=O)$_2$ R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like. Haloalkyl is a specific embodiment of substituted alkyl, wherein alkyl is substituted with one or more halogen atoms.

"Alkoxy" means an alkyl moiety attached through an oxygen bridge (i.e., —O-alkyl) such as —O-methyl, —O-ethyl, and the like.

"Thioalkyl" means an alkyl moiety attached through a sulfur bridge (i.e., —S-alkyl) such as —S-methyl, —S-ethyl, and the like.

"Alkylamino" and "dialkylamino mean one or two alkyl moieties attached through a nitrogen bridge (ie., —NHalkyl or —N(alkyl)(alkyl)) such as methylamino, ethylamino, dimethylamino, diethylamino, and the like.

"Hydroxyalkyl" means an alkyl substituted with at least one hydroxyl group.

Depending upon the A and X groups, representative compounds of this invention have one of the following structures (II) through (VI):

(II)
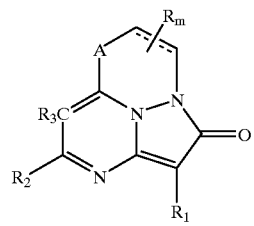

(III)
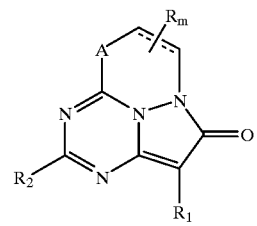

(IV)
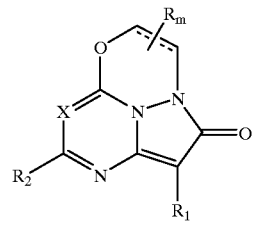

(V)
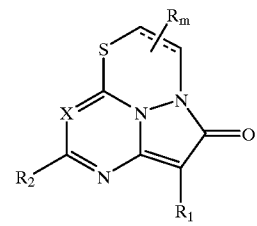

(VI)
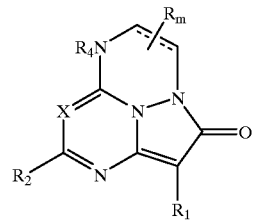

As used in the context of this invention,

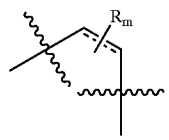

represents —CH$_2$CH$_2$— or —CH=CH— optionally substituted with 1, 2 or 3 R substituents (i.e., m=0, 1, 2 or 3). Accordingly, representative compounds of this invention include (but are not limited to) compounds having the following structures (1a) through (1i), where each occurrence of R is the same or different and represents a group (other than hydrogen) as defined previously:

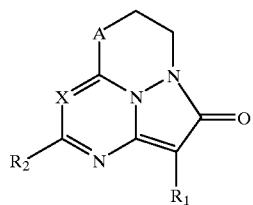
(1a)

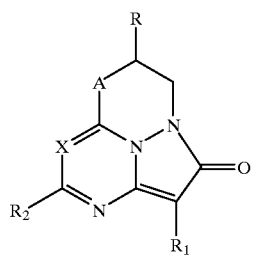
(1b)

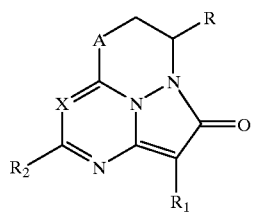
(1c)

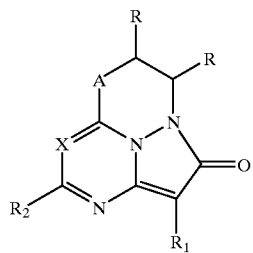
(1d)

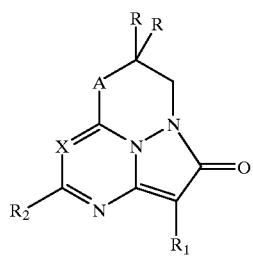
(1e)

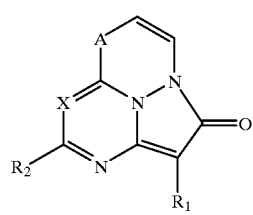
(1f)

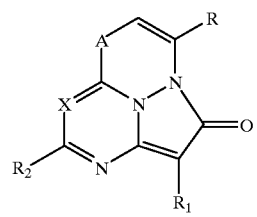
(1g)

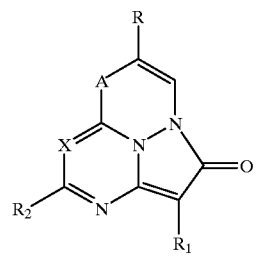
(1h)

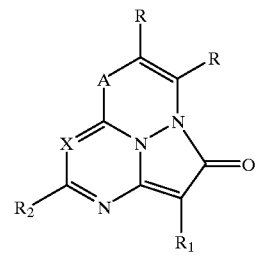
(1i)

When present, representative R groups of this invention include alkyl (such as methyl, ethyl, n-propyl, isopropyl and isobutyl), aryl (such as phenyl), heteroaryl (such as pyridyl), and alkylidenyl (such as $=CH_2$ and $=CHCH_3$). In the case of R being an alkylidenyl, the carbon atom to which it is attached must have the appropriate valency. For example, an alkuylidenyl moiety would not be appropriate at the R position shown in structure (1g) above.

In more specific embodiments of this invention, representative $R_1$ groups of this invention include (but are not limited to) 2,4-dichlorophenyl, 2,4-dimethyl-phenyl, 2-chloro-4-methylphenyl, 2-methyl-4-chlorophenyl, 2,4,6-trimethylphenyl, 2,4,5-trimethylphenyl, 2-chloro-4,5-dimethoxyphenyl, 2-chloro-4-methoxyphenyl, 2-methyl-4-methoxyphenyl, 2,4-dimethoxyphenyl, 2-trifluoromethyl-4-chlorophenyl, 3-methoxy-4-chlorophenyl, 2,5-dimethoxy-4-chlorophenyl, 2-methoxy-4-trifluoromethylphenyl, 2-methoxy-4-isopropylphenyl, 2-methoxy-4-trifluoromethylphenyl, 2-methoxy-4-isopropylphenyl 2-methoxy-4-methylphenyl, 4-methyl-6-dimethylaminopyridin-3-yl, 4-dimethylamino-6-methyl-pyridin-3-yl, 6-dimethylamino-pyridin-3-yl and 4-dimethylamino-pyridin-3-yl.

Similarly, representative $R_2$ groups include hydrogen methyl, ethyl, thiomethyl, trifluoromethyl and methoxy, representative $R_3$ groups include hydrogen, methyl, ethyl, chloro and fluoro, and representative $R_4$ groups include alkyl such as 4-heptyl, hexyl, pentyl and substituted alkyl such as methoxy or dimethoxy substituted propyl, pentyl and heptyl.

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In general, the compounds of structure (I) may be made according to the organic synthesis techniques known to those skilled in this field, as well as by the representative methods set forth in the Examples. For example, the synthesis of structure (I) may generally proceed according to the following Reaction Schemes 1 through 3.

Reaction Scheme 1

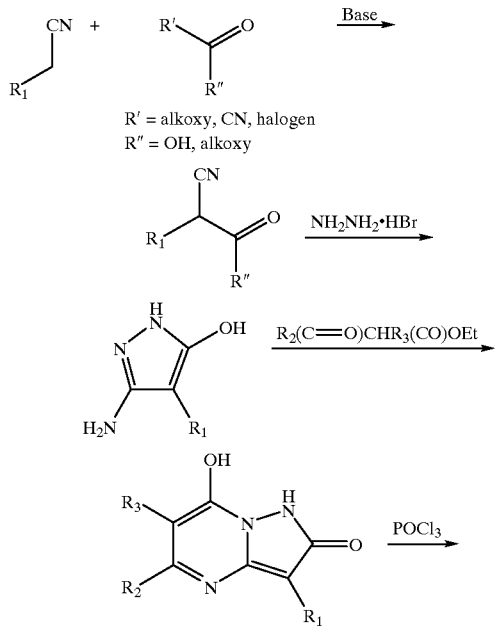

Reaction Scheme 2

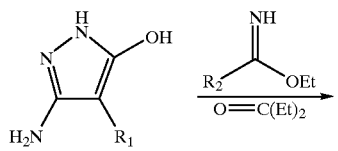

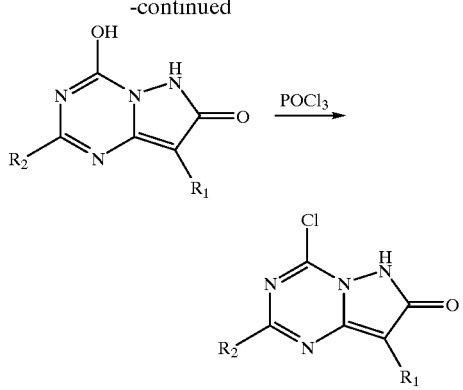

Reaction Scheme 3

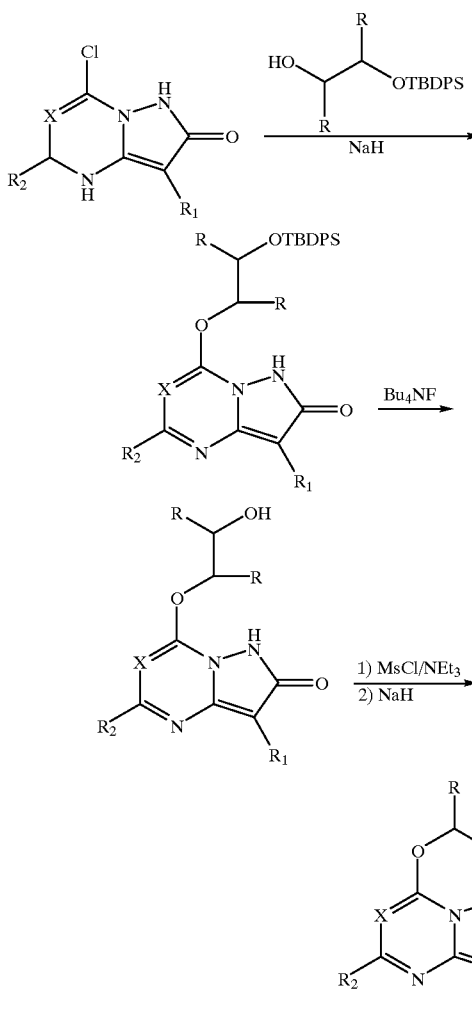

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., $[^{125}I]$ tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 $\mu$M. In a preferred embodiment of this invention, a CRF receptor antagonist has a $K_i$ of less than 1 $\mu$M, and more preferably less than 0.25 $\mu$M (i.e., 250 nM). As set forth in greater detail below, the $K_i$ values of representative compounds of this invention may be assayed by the methods set forth in Example 5.

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), pain, Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder—that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of an carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

In another embodiment, compounds of this invention and their analogs may be used as Positron Emission Tomography (PET) ligands, Single Photon Emission Computed Tomography (SPECT) ligands, or other diagnostic radiopharmaceutical agents. Incorporation of an appropriate isotope (such as $^{11}C$ or $^{18}F$ for PET or $125I$ in the case of SPECT) may provide an agent useful for the diagnosis or therapeutic management of a patient. In addition, use of a compound of the present invention may provide a physiological, functional, or biological assessment of a patient or provide disease or pathology detection and assessment.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, pain, Cushing's disease, infantile spasms, epilepsy, and substance abuse or withdrawal.

The following examples are provided for purposes of illustration, not limitation.

EXAMPLES

Representative CRF receptor antagonists of this invention may be prepared by the methods disclosed in Examples 1–4. Example 5 presents a method for determining the receptor binding activity ($K_i$), and Example 6 discloses an assay for screening compounds for CRF-stimulated adenylate cyclase activity.

EXAMPLE 1

SYNTHESIS OF REPRESENTATIVE COMPOUNDS

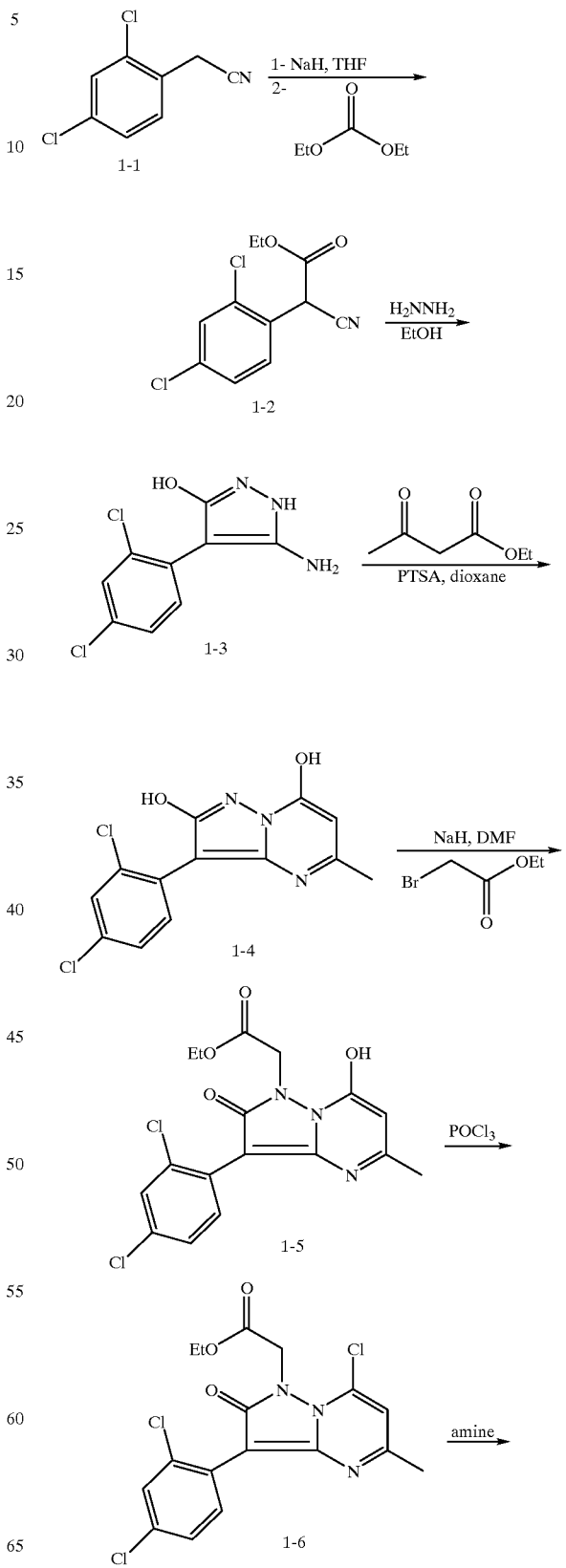

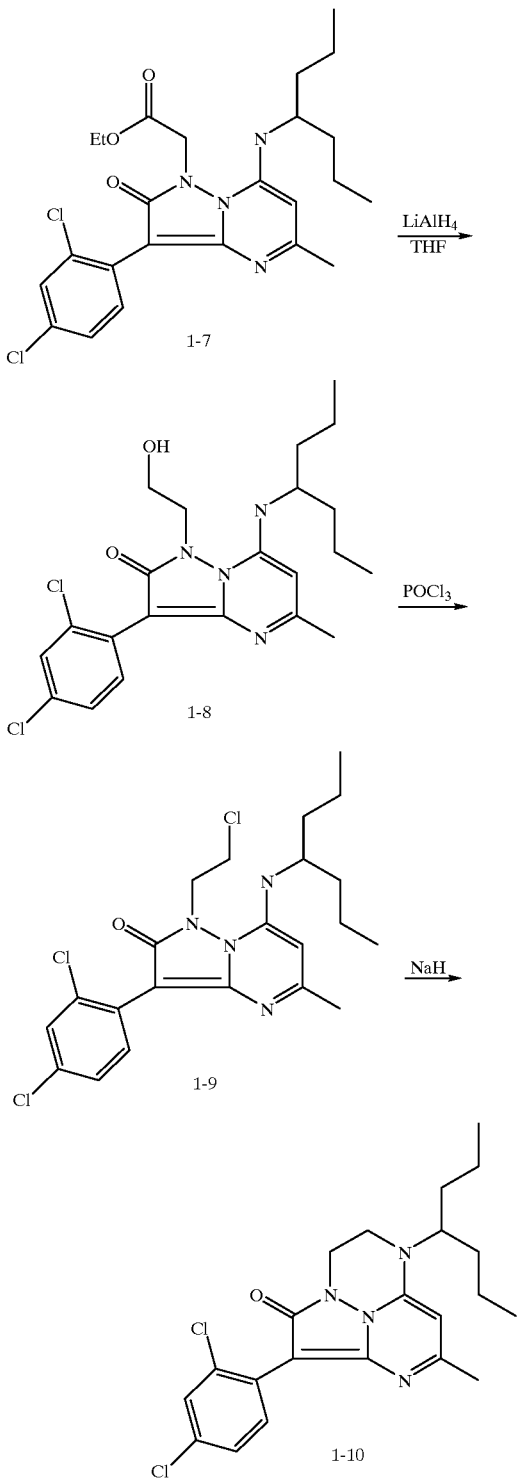

Compound 1-2

Dissolved 15 g of 2,4 dichlorophenylacetonitrile (1-1) in THF (60 mL). The solution was cooled to 0° C. and sodium hydride (60%, 4.19 grams, 1.3 equiv) and diethylcarbonate (12.72 mL, 1.3 equiv) were added slowly. The mixture was refluxed overnight. The product was seen by TLC ($R_f$ product=0.33, 20% EtOAc:Hexane) and by GC. The solution was cooled and 1N HCl was added until the mixture was slightly acidic. The mixture was extracted 3 times with 70 mL of ethyl acetate. The organic layer was washed with brine and dried with magnesium sulfate. Evaporation of excess solvent gave 18 g of an oily brown liquid 1-2.

Compound 1-3

Added 100 mL of 9:1 ethanol:water solution to compound 1-2. Hydrazine (2.2 mL, 1.0 equiv) was added and the mixture was refluxed overnight. Product by TLC stays on baseline with 50% ethylacetate:hexane solvent system. The ethanol was evaporated from the solution yielding a yellow solid. The solid was washed with approximately 100 mL of ether and was dried in an oven for 3 days to give 11.62 g of 1-3 (59% yield).

Compound 1-4

Dissolved 11.27 g of compound 1-3 in anhydrous dioxane (100 mL) and added 7.1 mL (1.2 equiv) of ethylacetoacetate and a few crystals of pTSA. The cloudy mixture was refluxed at 109° C. overnight. The solution was allowed to cool and a white solid settled to the bottom. The solid was filtered and washed 3× with ethyl ether. The solid was dried to give 14.48 g (58% yield) of white solid 1-4.

Compound 1-5

Added 10 mL of DMF to 1 g of compound 1-4 and heated until completely dissolved. The solution was cooled and sodium hydride (60% in oil, 0.19 g, 1.5 eq) and ethylbromoacetate (0.44 mL, 1.2 equiv) were added. The mixture was stirred under nitrogen for 3 hours. 1N HCl was added to the solution until the pH was approximately 7 and the mix was extracted with ethyl acetate (3×10 mL). The organic layer was washed with brine and dried with magnesium sulfate to yield 0.75 g of 1-5 as a white solid with an $R_f$ of 0.34 using 100% ethylacetate.

Compound 1-6

750 mg of compound 1-5 and 1 mL phoshorous oxychloride was heated overnight. Ice water and sodium bicarbonate were added until the reaction mixture was neutral. The mixture was extracted with ethyl acetate (3×). The organic layer was washed with brine and dried with magnesium sulfate. The resulting dark reddish/brown oil was filtered through a plug of silica gel. Compound 1-6 (0.56 g) was collected as a brown oil. TLC $R_f$ of 1-6 was 0.62 using a 1:1 solution of ethyl acetate:hexane.

Compound 1-7

Compound 1-6 was dissolved in 4 mL of anhydrous acetonitrile. 4-Heptylamine (2 mL) was added and the reaction mixture was refluxed at 90° C. for 5 hours. The reaction mixture was concentrated in vacuo, diluted with ethyl acetate and filtered through a silica gel plug. Concentration and drying overnight gave 0.502 g of product 1-7.

Compound 1-8

Anhydrous THF (2 mL) and 0.01 g (1.0 equiv) of lithium aluminum hydride were stirred under nitrogen. Compound 1-7 (250 mg) in 3 mL of THF was added and the solution was stirred for 1.5 hours then refluxed at 70° C. overnight. The THF was evaporated and the resulting mixture was diluted with water, neutralized with 1N HCl and extracted with ethyl acetate (3×10 mL). The organic layer was washed with brine and dried with magnesium sulfate to give 0.217g of compound 1-8.

Compound 1-9

A mixture of 1-8 (217 mg) and $POCl_3$ (4 mL) was refluxed overnight and then was stirred for 2 days. Ice water and sodium bicarbonate were added until the mixture was neutral followed by extraction with ethyl acetate. The organic layer was washed with brine then was dried with magnesium sulfate. Evaporation of solvent gave 181 mg of compound 1-9.

Compound 1-10

Compound 1-9 was dissolved in 5 mL of DMF. Sodium hydride (60% in oil, 0.016 g, 1 equiv) was added and the reaction was stirred under nitrogen for 24 hours. After 24 hours another equivalent of NaH was added. The reaction mixture was stirred for an additional 6 hours and the solvent was evaporated. Water and sodium bicarbonate were added until the mixture was neutral and the mixture was extracted with ethyl acetate (3×8 mL). The organic layer was washed with brine, dried over magnesium sulfate and concentrated in vacuo. Purification using a prep TLC plate and 30% ethyl acetate/hexane as elutant gave compound 1-10 (10.5 mg, MS ion=433).

EXAMPLE 2

SYNTHESIS OF REPRESENTATIVE COMPOUNDS

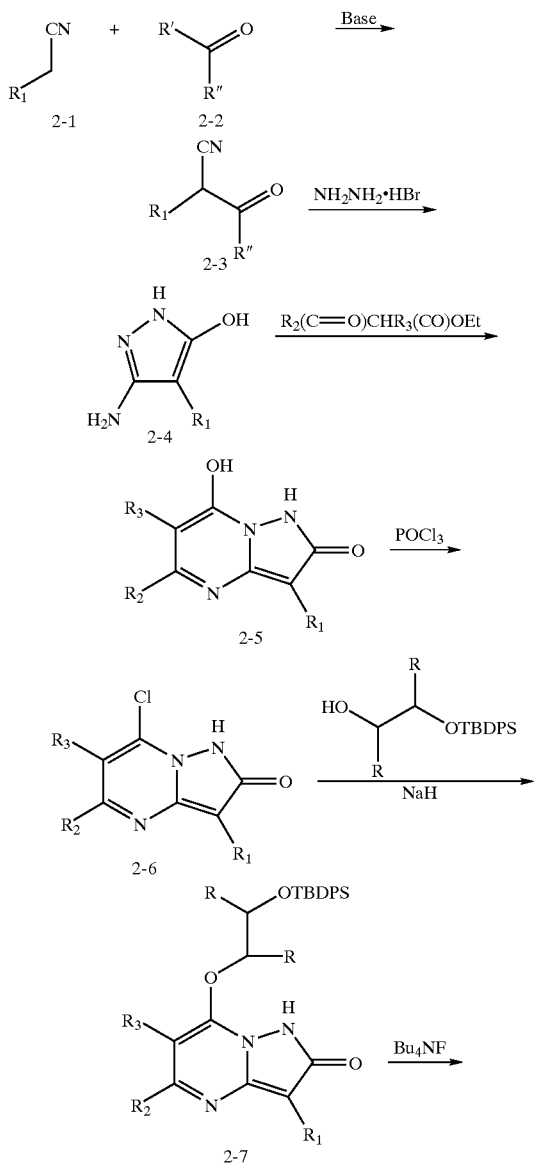

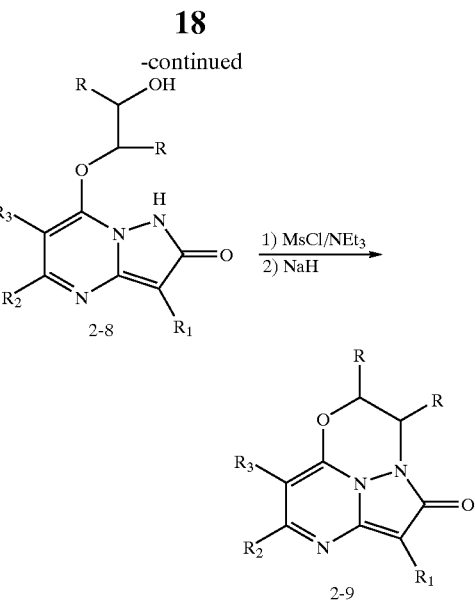

Compound 2-3

Sodium hydride (1.5 eq) is added to a solution of cyano compound 2-1 in THF. Compound 2-2 (R' is halogen, cyano, alkoxy; R" is OH, alkoxy; 1 eq) is added. The mixture is refluxed until no starting material is present. After return to room temperature, the mixture is treated with water. The two layers are separated. The aqueous layer is acidified with 1N HCl, cooled, and filtered to give compound 2-3.

Compound 2-4

A suspension of compound 2-3 and hydrazine.HBr (2 eq) in EtOH/H$_2$O (9/1) is heated at reflux for 0.5 hour. Ethanol is removed in vacuo and the residue is diluted with water. The aqueous phase is made basic with solid Na$_2$CO$_3$ and the product is extracted with ethyl acetate. The extract is dried with MgSO$_4$, filtered and concentrated in vacuo to give compound 2-4.

Compound 2-5

Compound 2-4 and substituted ethylacetoacetate (2 eq) in dioxane is heated at reflux for 20 hours. The suspension is cooled and ether is added. The solid is collected by filtration. Compound 2-5 is used as is in the next step.

Compound 2-6

Compound 2-5 is heated in acetonitrile with an excess of POCl$_3$. When the conversion is total, the solvent and excess of reagent are removed. The reaction mixture is neutralized and the product extracted with CH$_2$Cl$_2$. The organic layers are combined and are washed three times with water and brine. The organic phase is dried (MgSO$_4$) and concentrated in vacuo. Compound 2-6 is purified by silica gel chromatography.

Compound 2-7

Compound 2-6 is condensed with one equivalent of the t-butyldiphenyllsilyl protected diol in the presence of sodium hydride in dry DMF. The mixture is then heated at 50° C. for 6 hours. Upon cooling to room temperature the mixture is poured into saturated NH4Cl and is extracted with ethyl acetate. The organic layers are combined and washed three times with water and brine. The organic phase is dried (MgSO$_4$) and concentrated in vacuo. Purification via flash chromatography gives the desired product 2-7.

Compound 2-8

The silyl protected alcohol 2-7 is treated with 1 M Bu$_4$NF in THF. After 3 hours the mixture is washed with water and extracted with EtOAc. The organic phase is dried (MgSO$_4$) and concentrated in vacuo. Purification via flash chromatography gives the desired desilylated product 2-8.

Compound 2-9

The desilylated product 2-8 is then treated with methanesulfonyl chloride and triethylamine in $CH_2Cl_2$ at 0° C. After three hours the mixture is washed with saturated NH4Cl and brine. The organic phase is dried ($MgSO_4$) and concentrated in vacuo. Without further purification the mesylate is treated with NaH in THF at 0° C. After one hour the reaction mixture is poured into saturated NH4Cl and is extracted with EtOAc. The organic phase is dried ($MgSO_4$) and concentrated in vacuo. Purification via flash chromatography gives the desired product 9.

EXAMPLE 3

SYNTHESIS OF REPRESENTATIVE INTERMEDIATE

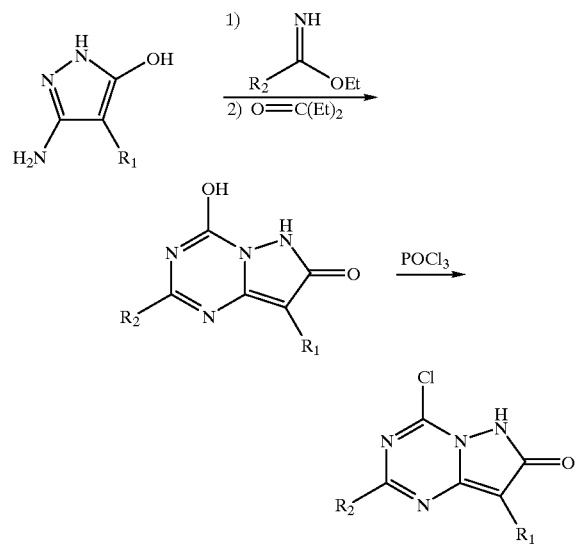

Compound 3-1

To 1.5eq. of $R_1C(NH)OEt$ and 1 eq of pyrazole in acetonitrile is added 1 eq of glacial acetic acid. The mixture is stirred at room temperature for 3 days. It is then concentrated and the precipitate is filtered off, washed with ether and dried. To an 1 eq NaOEt solution in ethanol is added 0.1 eq of the acetamidino solid and 0.8 eq of diethylcarbonate [R3=Et]. The mixture is heated at reflux for 18 hours. After cooling, solvent is removed. The residue is dissolved in water and a 1N HCl solution is added slowly until pH=5–6. The aqueous layer is extracted with EtOAc. The organic layers are combined, washed with brine, dried with $MgSO_4$ and the solvent evaporated to give the solid 3-1.

Compound 3-2

Compound 3-1 is heated in acetonitrile with an excess of $POCl_3$. When the conversion is total, the solvent and excess of reagent are removed. The reaction mixture is neutralized and the product extracted with $CH_2Cl_2$. The organic layers are combined and are washed three times with water and brine. The organic phase is dried ($MgSO_4$) and concentrated in vacuo. Compound 3-2 is purified by silica gel chromatography.

EXAMPLE 4

SYNTHESIS OF REPRESENTATIVE INTERMEDIATE

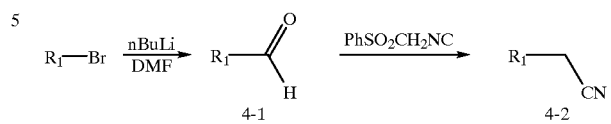

Compound 4-1

A solution of bromo compound $R_1$—Br (0.2 mol) in THF (400 mL) is cooled at −78° C. and is treated with BuLi (2.5 M, 88 mL, 0.22 mol) slowly. The mixture is stirred for 20 minutes at −78° C. and DMF (20.1 mL, 0.24 mol) is added dropwise. The mixture is stirred for 10 minutes, the cooling bath removed, and the reaction is allowed to warm to room temperature. Water is added and the aqueous mixture is extracted with ethyl acetate, washed with brine, dried over $MgSO_4$ and concentrated in vacuo to give 4-1.

Compound 4-2

A solution of tosylmethyl isocyanide (15.4 g) in dimethoxyethane (50 mL) is added dropwise into a suspension of KOBu-t (10.16 g, 90 immol) in dimethoxyethane (50 mL) at −60° C. After 10 minutes, a solution of aldehyde 4-1 (67 mmol) in dimethoxyethane (75 mL) is added dropwise. The mixture is stirred at −50° C. for 30 minutes and is quenched with methanol (200 mL). The mixture is refluxed for 1 hour, the solvent evaporated and the residue partitioned in ethyl acetate/water. The organic layer is washed with water, dried over $MgSO_4$, and filtered through a silica pad, eluting with ethyl acetate. The ethyl acetate is concentrated in vacuo giving compound 4-2 (62 mmol) as an oil. This compound may be used as the starting material in Examples 1 and 2 (ie., compounds 1-1 and 2-1).

EXAMPLE 5

CRF Receptor Binding Activity

The compounds of this invention may be evaluated for binding activity to the CRF receptor by a standard radioligand binding assay as generally described by DeSouza et al. (J. Neurosci. 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 ml Eppendorf tubes using approximately $1 \times 10^6$ cells per tube stably transfected with human CRF receptors. Each tube receives about 0.1 ml of assay buffer (e.g., Dulbecco's phosphate buffered saline, 10 mM magnesium chloride, 20 $\mu$M bacitracin) with or without unlabeled sauvagine, urotensin I or CRF (final concentration, 1 $\mu$M) to determine nonspecific binding, 0.1 ml of [125I] tyrosine-ovine CRF (final concentration ~200 pM or approximately the $K_D$ as determined by Scatchard analysis) and 0.1 ml of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the non-linear least-square curve-fitting program LIGAND of Munson and Rodbard (*Anal. Biochem.* 107:220, 1990).

EXAMPLE 6

CRF-stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (Synapse 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 µl of a solution of 95% ethanol and 20 mM aqueous hydrochloric acid is added to each well and the resulting suspensions are incubated at −20° C. for 16 to 18 hours. The solution is removed into 1.5 ml Eppendorf tubes and the wells washed with an additional 200 µl of ethanol/aqueous hydrochloric acid and pooled with the first fraction. The samples are lyophilized and then resuspended with 500 µl sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds ($10^{-12}$ to $10^{-6}$ M).

It will be appreciated that, although specific embodiments of the invention have been described herein for purposes of illustration, various modifications may be made without departing from the spirit and scope of the invention. Accordingly, the invention is not limited except as by the appended claims.

What is claimed is:
1. A compound having the following structure:

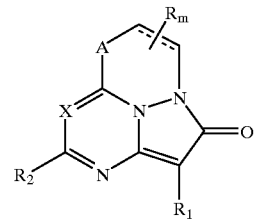

or a stereoisomer or pharmaceutically acceptable salt thereof,
wherein:
X is nitrogen or $CR_3$;
A is O, S or $NR_4$;
"———" represents an optional double bond;
R is an optional substituent which, at each occurrence, is independently alkyl, aryl, heteroaryl, alkylidenyl, arylalkyl or heteroarylalkyl, wherein m is 0, 1, 2 or 3 and represents the number of R substituents; wherein, when R is a monovalent substituent, it is single-bonded to the ring, and when R is a divalent substituent, it is double-bonded to the ring.
$R_1$ is alkyl substituted alkyl, aryl, substituted aryl, heteroaryl or substituted heteroaryl;
$R_2$ is hydrogen, halogen, cyano, alkyl, substituted alkyl, alkoxy or thioalkyl;
$R_3$ is hydrogen, halogen, alkyl or substituted alkyl; and
$R_4$ is hydrogen, alkyl, substituted alkyl, aryl, substituted aryl, heterocycle or substituted heterocycle.
2. The compound of claim 1 wherein A is O.
3. The compound of claim 1 wherein A is S.
4. The compound of claim 1 wherein A is $NR_4$.
5. The compound of claim 1 wherein X is nitrogen.
6. The compound of claim 1 wherein X is $CR_3$.
7. The compound of claim 1 wherein $R_1$ is substituted aryl.
8. The compound of claim 1 wherein $R_1$ is substituted phenyl.
9. The compound of claim 1 wherein $R_2$ is alkyl.
10. The compound of claim 1 wherein m is 0.
11. A composition comprising a compound of claim 1 in combination with a pharmaceutically acceptable carrier or diluent.
12. A method for treating a disorder manifesting hypersecretion of CRF in a warm-blooded animal, comprising administering to the animal an effective amount of the composition of claim 11.
13. The method of claim 12 wherein the disorder is stroke.
14. The method of claim 12 wherein the disorder is depression.
15. The method of claim 12 wherein the disorder is anxiety.

* * * * *

UNITED STATES PATENT AND TRADEMARK OFFICE
CERTIFICATE OF CORRECTION

PATENT NO.    : 6,541,469 B2
DATED         : April 1, 2003
INVENTOR(S)   : Mustapha Haddach It is certified that error appears in the above-identified patent and that said Letters Patent is hereby corrected as shown below:

<u>Column 22,</u>
Line 19, " "——" represents an optional double bond;" should read as -- "---" represents an optional double bond; --.

Signed and Sealed this

First Day of July, 2003

JAMES E. ROGAN
*Director of the United States Patent and Trademark Office*